(12) United States Patent
Ketelhohn et al.

(10) Patent No.: US 11,191,553 B2
(45) Date of Patent: Dec. 7, 2021

(54) CONNECTOR FOR SURGICAL HANDPIECE

(71) Applicant: Integra LifeSciences NR Ireland Limited, Dublin (IE)

(72) Inventors: Robert A. Ketelhohn, Dunstable, MA (US); Daniel J. Cotter, North Easton, MA (US); Prakash Manandhar, Lawrence, MA (US); John Bertorelli, Andover, MA (US); Saurav V. Gupta, Medway, MA (US); Erin-Anne A. Lemieux, Mont Vernon, NH (US)

(73) Assignee: INTEGRA LIFESCIENCES ENTERPRISES, LLLP, Princeton, NJ (US)

( * ) Notice: Subject to any disclaimer, the term of this patent is extended or adjusted under 35 U.S.C. 154(b) by 7 days.

(21) Appl. No.: 15/621,300

(22) Filed: Jun. 13, 2017

(65) Prior Publication Data

US 2017/0354429 A1 Dec. 14, 2017

Related U.S. Application Data

(63) Continuation of application No. 29/567,765, filed on Jun. 13, 2016, now Pat. No. Des. 820,441.

(51) Int. Cl.
*A61B 17/22* (2006.01)
*A61M 3/02* (2006.01)
(Continued)

(52) U.S. Cl.
CPC ..... *A61B 17/22012* (2013.01); *A61M 1/0058* (2013.01); *A61M 1/86* (2021.05);
(Continued)

(58) Field of Classification Search
CPC .............. A61M 1/0058; A61M 1/0086; A61M 3/0279; A61M 39/10; A61M 39/1011;
(Continued)

(56) References Cited

U.S. PATENT DOCUMENTS 1,615,595 A * 1/1927 O'connor ................ F16L 37/24
285/88
1,869,411 A * 8/1932 De Mooy ............... F16L 37/42
137/613
(Continued)

FOREIGN PATENT DOCUMENTS

CN 102802692 A 11/2012
CN 104548331 A 4/2015
(Continued)

OTHER PUBLICATIONS

Partial Search for International Application No. PCT/IB2017/057145 dated Jan. 31, 2018.
(Continued)

*Primary Examiner* — William R Carpenter
*Assistant Examiner* — William R Frehe
(74) *Attorney, Agent, or Firm* — Middleton Reutlinger

(57) ABSTRACT

A surgical handpiece nosecone having an end overmold portion and/or an internal overmold portion. The end overmold portion is located at an end of the nosecone and compressed between the surgical handpiece housing and nosecone. The internal overmold portion is positioned radially about the nosecone on the inner surface to provide a fluid tight seal that prevents ingress of irrigation fluid into the housing.

9 Claims, 12 Drawing Sheets

Related U.S. Application Data

(60) Provisional application No. 62/421,645, filed on Nov. 14, 2016, provisional application No. 62/394,994, filed on Sep. 15, 2016.

(51) Int. Cl.
  *A61M 1/00* (2006.01)
  *A61M 39/10* (2006.01)
  *F16L 37/252* (2006.01)

(52) U.S. Cl.
  CPC .. *A61M 3/0279* (2013.01); *A61B 2017/22014* (2013.01); *A61B 2017/22025* (2013.01); *A61B 2017/22079* (2013.01); *A61B 2217/007* (2013.01); *A61M 39/10* (2013.01); *F16L 37/252* (2013.01)

(58) Field of Classification Search
  CPC .. A61M 2039/1016; A61M 2039/1027; A61M 2039/1033; A61M 2039/1038; A61M 39/1055; F16L 37/252
  See application file for complete search history.

(56) References Cited

U.S. PATENT DOCUMENTS

| | | | |
|---|---|---|---|
| 3,583,667 A * | 6/1971 | Amneus, Jr. | F16L 37/252 251/149.5 |
| 4,033,613 A * | 7/1977 | Bram | F16L 37/252 285/184 |
| 4,063,557 A | 12/1977 | Wuchinich et al. | |
| 4,223,676 A | 9/1980 | Wuchinich et al. | |
| 4,425,115 A | 1/1984 | Wuchinich | |
| 4,516,398 A | 5/1985 | Wuchinich | |
| 4,580,816 A * | 4/1986 | Campbell | A61M 39/00 285/321 |
| 4,634,419 A | 1/1987 | Kreizman et al. | |
| 4,734,964 A | 4/1988 | Lane et al. | |
| 4,747,820 A * | 5/1988 | Hornlein | A61B 17/320068 604/22 |
| 4,750,902 A | 6/1988 | Wuchinich et al. | |
| 4,768,496 A | 9/1988 | Kreizman et al. | |
| 4,827,911 A | 5/1989 | Broadwin et al. | |
| 4,846,790 A | 7/1989 | Hornlein et al. | |
| 4,881,761 A | 11/1989 | Hornlein et al. | |
| 4,921,476 A | 5/1990 | Wuchinich | |
| 4,931,047 A | 6/1990 | Broadwin et al. | |
| 4,978,333 A | 12/1990 | Broadwin et al. | |
| 4,988,334 A | 1/1991 | Hornlein et al. | |
| 5,015,227 A | 5/1991 | Broadwin et al. | |
| 5,190,517 A | 3/1993 | Zieve et al. | |
| 5,221,282 A | 6/1993 | Wuchinich | |
| 5,222,937 A | 6/1993 | Kagawa | |
| 5,421,829 A | 6/1995 | Olichney et al. | |
| 5,466,020 A * | 11/1995 | Page | F16L 37/252 285/361 |
| 5,484,398 A | 1/1996 | Stoddard | |
| D367,323 S | 2/1996 | Carr | |
| 5,492,528 A | 2/1996 | Anis | |
| 5,984,904 A | 11/1999 | Steen et al. | |
| 6,083,191 A | 7/2000 | Rose | |
| 6,117,151 A | 9/2000 | Urich et al. | |
| 6,177,755 B1 | 1/2001 | Hur | |
| D438,952 S | 3/2001 | Cimino et al. | |
| 6,214,017 B1 | 4/2001 | Stoddard et al. | |
| 6,256,859 B1 | 7/2001 | Stoddard et al. | |
| 6,319,223 B1 | 11/2001 | Wortrich | |
| 6,468,059 B2 | 10/2002 | Haser | |
| 6,499,358 B1 | 12/2002 | Hogan et al. | |
| D477,867 S | 7/2003 | O'Mahony | |
| 6,595,957 B1 | 7/2003 | Griffiths | |
| 6,602,227 B1 | 8/2003 | Cimino et al. | |
| D479,320 S | 9/2003 | O'Mahony | |
| 6,654,999 B2 | 12/2003 | Stoddard et al. | |
| 6,723,110 B2 | 4/2004 | Timm et al. | |
| 7,204,825 B2 | 4/2007 | Cimino et al. | |
| D557,803 S | 12/2007 | Muri | |
| D557,804 S | 12/2007 | Muri | |
| 7,442,168 B2 | 10/2008 | Novak et al. | |
| 7,871,392 B2 | 1/2011 | Sartor | |
| 8,092,475 B2 * | 1/2012 | Cotter | A61B 17/1604 606/169 |
| 8,118,823 B2 | 2/2012 | Cotter et al. | |
| 8,142,460 B2 | 3/2012 | Cotter et al. | |
| 8,211,103 B2 | 7/2012 | Greep | |
| D675,728 S | 2/2013 | Tout | |
| 8,518,066 B2 | 8/2013 | Cotter et al. | |
| D699,836 S | 2/2014 | Burger | |
| 9,149,291 B2 | 10/2015 | Parham et al. | |
| 9,421,027 B2 | 8/2016 | Cotter et al. | |
| 2002/0002369 A1 | 1/2002 | Hood | |
| 2006/0052774 A1 * | 3/2006 | Garrison | A61B 18/042 606/42 |
| 2006/0063973 A1 | 3/2006 | Makower et al. | |
| 2008/0200884 A1 | 8/2008 | Perkins et al. | |
| 2011/0160620 A1 | 6/2011 | Gill et al. | |
| 2013/0184688 A1 * | 7/2013 | Gagliardoni | A61M 39/1011 604/535 |
| 2013/0331872 A1 | 12/2013 | Ray et al. | |
| 2014/0135804 A1 | 5/2014 | Weisenburgh, II | |
| 2015/0080925 A1 | 3/2015 | Schulte et al. | |
| 2015/0119819 A1 * | 4/2015 | Guala | B29C 45/14344 604/244 |
| 2015/0328048 A1 | 11/2015 | Koplin | |
| 2016/0169432 A1 * | 6/2016 | Proulx-Croteau | F16L 37/252 285/307 |
| 2017/0268709 A1 * | 9/2017 | Gibson | F16L 37/252 |
| 2017/0304655 A1 | 10/2017 | Cotter et al. | |
| 2017/0333606 A1 | 11/2017 | Manandhar et al. | |
| 2017/0354429 A1 | 12/2017 | Ketelhohn et al. | |
| 2019/0159793 A1 | 5/2019 | Cotter et al. | |

FOREIGN PATENT DOCUMENTS

| | | |
|---|---|---|
| CN | 104797289 A | 7/2015 |
| EP | 1607075 | 12/2005 |
| JP | S63503041 A | 11/1988 |
| JP | H0194841 A | 4/1989 |
| JP | H0199547 A | 4/1989 |
| JP | H10511759 A | 11/1998 |
| JP | 2002280119 A | 9/2002 |
| WO | 8706116 A1 | 10/1987 |
| WO | 9308750 A2 | 5/1993 |
| WO | 9415539 A2 | 7/1994 |
| WO | 9517855 | 7/1995 |
| WO | 9825542 A2 | 6/1998 |
| WO | 2004026150 A2 | 4/2004 |
| WO | 2004045705 | 6/2004 |
| WO | 2008154803 A1 | 12/2008 |
| WO | 2010057211 A1 | 5/2010 |
| WO | 2011005467 A2 | 1/2011 |
| WO | 2014134292 | 9/2014 |
| WO | 2015061258 | 4/2015 |
| WO | 2017187345 | 11/2017 |
| WO | 2017203408 | 11/2017 |
| WO | 2018051196 | 3/2018 |
| WO | 2018051196 A1 | 3/2018 |

OTHER PUBLICATIONS

European Patent Office, International Search Report and Written Opinion for PCT/IB2017/057145 dated Mar. 15, 2018, dated Mar. 23, 2018, Rijswijk, NL.
Transmittal Letter of Related Cases dated Jan. 30, 2019.
International Search Report and Written Opinion for PCT/IB2017/052382 dated Aug. 17, 2017.
International Search Report and Written Opinion for PCT/IB2017/052980 dated Jul. 19, 2017.
International Search Report and Written Opinion for PCT/IB2017/053510 dated Nov. 13, 2017.
Partial Search Report for PCT/IB2017/053510 dated Sep. 22, 2017.

(56) References Cited

OTHER PUBLICATIONS

Franasiak, Jason M.; Ergonomic Strain in Minimally Invasive Surgery: Addressing the Strain Epidemic www.jcomjournal.com; vol. 22, No. 6, pp. 267-273, Jun. 2015.
Krautkramer J. and Krautkramer H., Ultrasonic Testing of Materials, 1983.
Berguer, R.; Ergonomic problems associated with laparoscopic surgery; Surgical Endoscopy, 1999 13: 466-468; 1999.
Integra Lifesciences Corporation; CUSA Excel Ultrasonic Surgical Aspiration System, CUSA EXcel System User's Guide, 6 pages, 2007.
Integra Lifesciences Corporation; CUSA Excel+ Ultrasonic Surgical Aspirator, 8 pages, 2012.
SonaStar; Ultrasonic surgical aspiration system; Accuracy Matters, 2015.
European Patent Office, International Search Report and Written Opinion for PCT/IB2020/050713 dated Mar. 30, 2020, 15 pages.
International Preliminary Report on Patentability for application No. PCT/IB2020/050713 dated Jul. 27, 2021.
Japan Patent Office, Notice of Reasons for Rejection for app. No. 2019-512218 dated Aug. 12, 2021.

* cited by examiner

SECTION A-A

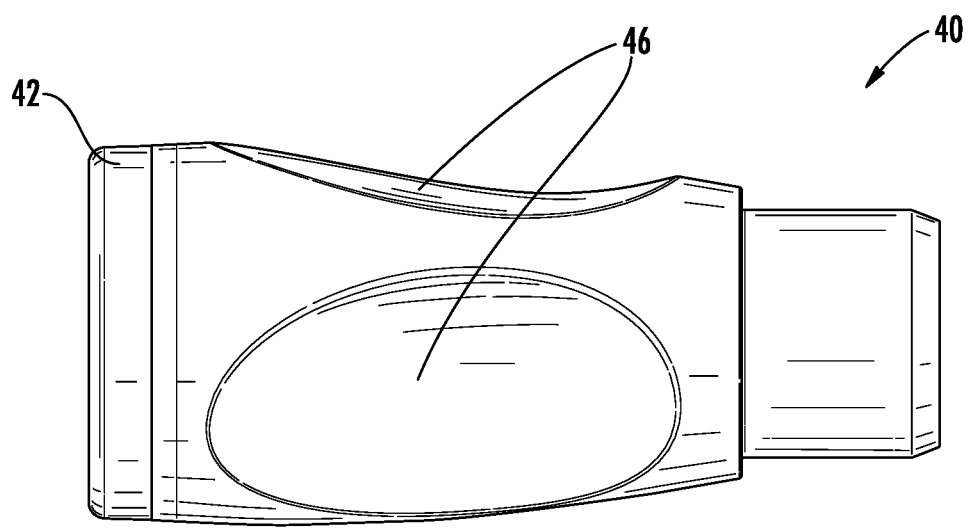
FIG. 10
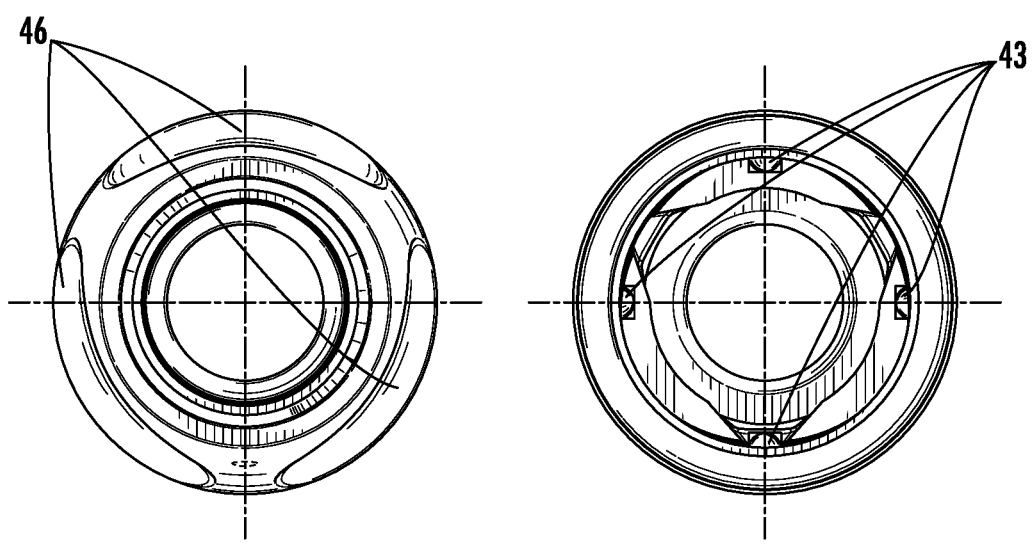
FIG. 11     FIG. 12

SECTION B-B

SECTION C-C

SECTION D-D

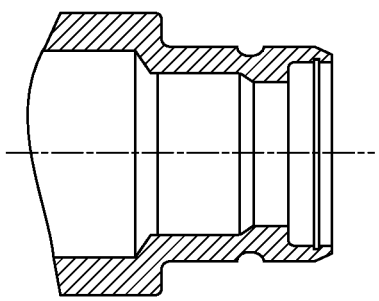
SECTION F-F
*FIG.* 22
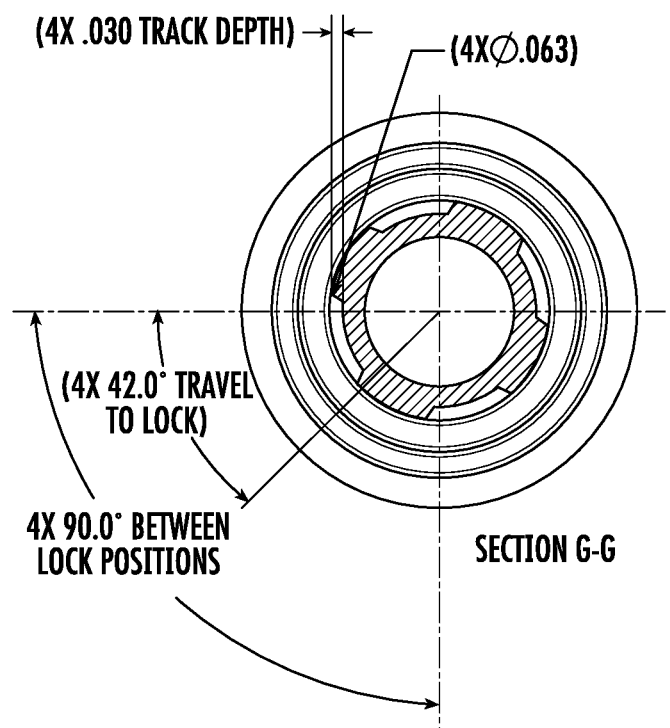
SECTION G-G
*FIG.* 23

CONNECTOR FOR SURGICAL HANDPIECE

CROSS-REFERENCE TO RELATED APPLICATIONS

This application claims priority to and benefit under 35 U.S.C. § 119 to U.S. Provisional Application No. 62/421,645, filed Nov. 14, 2016 and U.S. Provisional Application No. 62/394,994, filed Sep. 15, 2016, and also to U.S. Design application 29/567,765, filed Jun. 13, 2016, the entire contents of each of which are hereby incorporated by reference.

BACKGROUND OF THE INVENTION

Embodiments of the present invention relate generally to connectors for surgical handpieces, for example, handpieces in ultrasonic surgical aspirator systems for tissue ablation.

Ultrasonic aspiration has become the standard of care for removal of tumors and diseased tissue in neurosurgery and general surgery. Ultrasonic aspirators are used for ultrasonic fragmentation of tissue at an operation site and aspiration of the tissue particles and fluid away from the site. Typically, ultrasonic surgical aspirators include an ultrasonic transducer supported within a handpiece, an ultrasonically vibrating horn or tip operably connected to the ultrasonic transducer, and a sleeve or flue positioned about the horn. The horn includes a longitudinally extending central bore having one end located adjacent a distal tip and a second end located adjacent the proximal end of the horn. The proximal end of the horn is adapted to engage a vacuum source to facilitate aspiration of fluid. The flue is positioned about the horn to define an annular passage. Irrigation fluid is supplied through the annular passage around the horn to the surgical site where it mixes with blood and tissue particles and is aspirated through the bore in the horn. By mixing the irrigation fluid with the blood and tissue particles, coagulation of the blood is slowed down and aspiration thereof is aided. When the longitudinally vibrating tip in such an aspirator is brought into contact with tissue, it gently, selectively, and precisely fragments and removes the tissue. U.S. Pat. Nos. 5,015,227 and 4,988,334 disclose such ultrasonic surgical devices and are incorporated herein by reference. A known ultrasonic aspirator on the market is the CUSA® Excel Ultrasonic Surgical Aspirator (Integra LifeSciences Corporation, Plainsboro, N.J., U.S.A.).

Examples of existing handpieces include CUSA Excel 23 kHz and 36 kHz Handpieces (Integra LifeSciences Corporation, Plainsboro, N.J., U.S.A.) and those described in U.S. Pat. Nos. 4,223,676, 4,425,115 and 6,214,017. Those existing handpieces require user installed O-rings to provide sealing, support, and clasping functionality for the nosecone. The O-rings need to be installed by the user with each surgical procedure. The O-rings are small and difficult to install in operating room by practitioners wearing gloves, and the O-rings can be placed incorrectly or on the wrong mating geometry. In addition, the O-rings are different in diameter and could be selected and installed incorrectly. The O-rings for different handpieces could be selected incorrectly in manufacturing and assembly. In other existing devices, O-ring seals may be reusable and sterilizable but require periodic maintenance, and thus raise some concerns on ability to clean and sterilize over life.

Hence, those skilled in the art have recognized a need for a surgical handpiece connector with improved ease of use. Embodiments of the present invention fulfill this need and others.

SUMMARY OF THE INVENTION

Briefly and in general terms, embodiments of the present invention provide a connector for surgical handpiece, such as a nosecone, that incorporates an overmolding technology. More specifically, the nosecone eliminates user installed O-rings and enhances ease of use. The J-lock clasp of the nosecone and its seal is incorporated to a single proximal overmolded soft polymer and the distal diametrical seal is accomplished with a separate overmolded ring seal.

In some embodiments of the invention, for example, a connection apparatus for attachment of members of a medical device may comprise a first member having a first body and a first connecting section. In various embodiments, the first connecting section may have a first end face and an inner surface. In some embodiments, a second member may have a second body, a second connecting section and a shoulder at the junction between the second body and the second connecting section. Moreover, in some embodiments, the second connecting section may have a second end face and an outer surface shaped for telescoping into the first connecting section. In various embodiments, the outer surface may have a groove extending from the second end face towards the shoulder. In some embodiments, the first member may have a nub on the inner surface extending radially inward for engaging the groove. In various embodiments, the first member may have an end overmold portion at least partially covering the first end face and positioned to bear against the shoulder, whereby the end overmold portion may be compressed between the first body and the second body.

In addition, in various embodiments, the first member may have more than one nub on the inner surface arranged radially about the first connecting section, and the second member may have more than one groove on the outer surface arranged radially about the second connecting section, and each nub may be positioned to engage with each groove. In some embodiments, the end overmold portion may be made of a thermoplastic elastomer. In various embodiments, the first member may be a nosecone and the second member may be a surgical handpiece housing. Moreover, in some embodiments, the groove may be J-shaped. In various embodiments, the nub may be sphere-shaped. In some embodiments, the connection apparatus may comprise an internal overmold portion positioned radially about the inner surface of the first member.

In various embodiments, a method for attaching members of a medical device may comprise the steps of providing a first member having a first body and a first connecting section. In some embodiments, the first connecting section may have a first end face, an inner surface, a nub on the inner surface extending radially inward, and an end overmold portion at least partially covering the first end face. In various embodiments, the method may include providing a second member having a second body, a second connecting section and a shoulder at the junction between the second body and the second connecting section, the second connecting section may have a second end face and an outer surface, the outer surface may have a groove extending from the second end face towards the shoulder. In some embodiments, the method may include telescoping the second connecting section into the first connecting section. In various embodiments, the method may include locating the groove in the outer surface of the second connecting section. Moreover, in some embodiments, the method may include positioning the nub to engage the groove and moving the nub in the groove towards the shoulder until the end overmold portion contacts the shoulder whereby the end overmold portion may be compressed between the first body and the second body.

In some embodiments, the method may include providing more than one nub on the inner surface radially about the first connecting section. In various embodiments, the method may include providing more than one groove on the outer surface arranged radially about the second connecting section, wherein each nub may be positioned to engage with each groove. In some embodiments, the method may include positioning each nub to engage each groove. Moreover, in some embodiments, the method may include moving each nub in each groove towards the shoulder until the end overmold portion contacts the shoulder. In addition, in some embodiments, the overmold portion may be made of a thermoplastic elastomer. In some embodiments, the first member may be a nosecone and the second member may be a surgical handpiece housing. In various embodiments, the groove may be J-shaped. In some embodiments, the nub may be sphere-shaped. Moreover, in some embodiments, an internal overmold portion may be positioned radially about the inner surface of the first member.

In various embodiments, an ultrasonic aspirator apparatus for fragmenting tissue and removing fragmented tissue may include a surgical handpiece comprising a housing, a nosecone attached to the housing, and a transducer mounted within the housing. In some embodiments, a surgical tip may be connected to the transducer. In various embodiments, an irrigation system may be connected to the handpiece for supplying irrigation fluid adjacent the surgical site for suspending fragmented tissue. In some embodiments, an aspirating system may be connected to the handpiece for aspirating fluid and tissue fragmented at the surgical site. Moreover, in some embodiments, the nosecone may have an inner surface and an outer surface, and has an internal overmold portion on the inner surface may be positioned radially about the nosecone to provide a fluid tight seal that prevents ingress of irrigation fluid into the housing.

In addition, in various embodiments, the nosecone may further comprise an end overmold portion in contact with the housing to provide a seal between the housing and the nosecone. In some embodiments, the nosecone may comprise at least one nub on an inner surface extending radially inward. In various embodiments, the housing may be configured to attach to the nosecone and may have a groove on an outer surface extending proximally from a distal end of the housing. Further, in some embodiments, the nosecone may further comprise an end overmold portion at least partially covering a proximal end of the nosecone and positioned to bear against the housing. In various embodiments, the internal overmold portion may be made of a thermoplastic elastomer. In some embodiments, the nosecone may have a plurality of recessed lobes on the outer surface, the lobes being circumferentially spaced about a longitudinal axis. In various embodiments, the nosecone may have three recessed lobes spaced symmetrically on the outer surface to be grasped by a user.

In accordance with aspects of some embodiments of the invention, there is provided a connection apparatus for attachment of members of a medical device. The connection apparatus comprises a first member having a first body and a first connecting section, the first connecting section having a first end face and an inner surface; a second member having a second body, a second connecting section and a shoulder at the junction between the second body and the second connecting section, the second connecting section having a second end face and an outer surface shaped for telescoping into the inner surface of the first connecting section, the outer surface having a groove extending from the second end face towards the shoulder; wherein the first member has a nub on the inner surface extending radially inward for engaging the groove; and wherein the first member has an end overmold portion at least partially covering the first end face and positioned to bear against the shoulder, whereby the end overmold portion is compressed between the first body and the second body.

In more detailed aspects, in the connection apparatus, the first member has more than one nub on the inner surface arranged radially about the first connecting section, and the second member has more than one groove on the outer surface arranged radially about the second connecting section, and each nub is positioned to engage with each groove.

In accordance with other aspects of embodiments of the present invention, a method for attaching members of a medical device is provided. The method comprises providing a first member having a first body and a first connecting section, the first connecting section having a first end face, an inner surface, a nub on the inner surface extending radially inward, and an end overmold portion at least partially covering the first end face; providing a second member having a second body, a second connecting section and a shoulder at the junction between the second body and the second connecting section, the second connecting section having a second end face and an outer surface, the outer surface having a groove extending from the second end face towards the shoulder; telescoping the second connecting section into the first connecting section; locating the groove in the outer surface of the second connecting section; positioning the nub to engage the groove; and moving the nub in the groove towards the shoulder until the end overmold portion contacts the shoulder whereby the end overmold portion is compressed between the first body and the second body.

In accordance further aspects of embodiments of the present invention, there is provided an ultrasonic aspirator apparatus for fragmenting tissue and removing fragmented tissue. The ultrasonic aspirator apparatus comprises a surgical handpiece comprising a housing, a nosecone attached to the housing, and a transducer mounted within the housing; a surgical tip connected to the transducer; an irrigation system connected to the handpiece for supplying irrigation fluid adjacent the surgical site for suspending fragmented tissue; and an aspirating system connected to the handpiece for aspirating fluid and tissue fragmented at the surgical site; wherein the nosecone has an inner surface and an outer surface, and has an internal overmold portion on the inner surface positioned radially about the nosecone to provide a fluid tight seal that prevents ingress of irrigation fluid into the housing. The ultrasonic aspirator apparatus may additionally comprise an end overmold portion in contact with the housing to provide a seal between the housing and the nosecone.

In further detailed aspects, the nosecone may have a plurality of recessed lobes on the outer surface, the lobes being circumferentially spaced about a longitudinal axis. For example, the nosecone may have a tri-lobe configuration on the outer surface to be grasped by a user.

Other features and advantages of the embodiments of the present invention will become more apparent from the following detailed description of the embodiments, when taken in conjunction with the accompanying exemplary drawings.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

Embodiments of the present invention are described herein with reference to the drawings, in which:

FIG. 10 is a front elevational view thereof;

FIG. 11 is a distal end view thereof;

FIG. 12 is a proximal end view thereof;

FIG. 22 is a cross-sectional view taken along line F-F of FIG. 20;

FIG. 23 is a cross-sectional view taken along line G-G of FIG. 20;

DETAILED DESCRIPTION OF THE PREFERRED EMBODIMENTS

Figure 1:
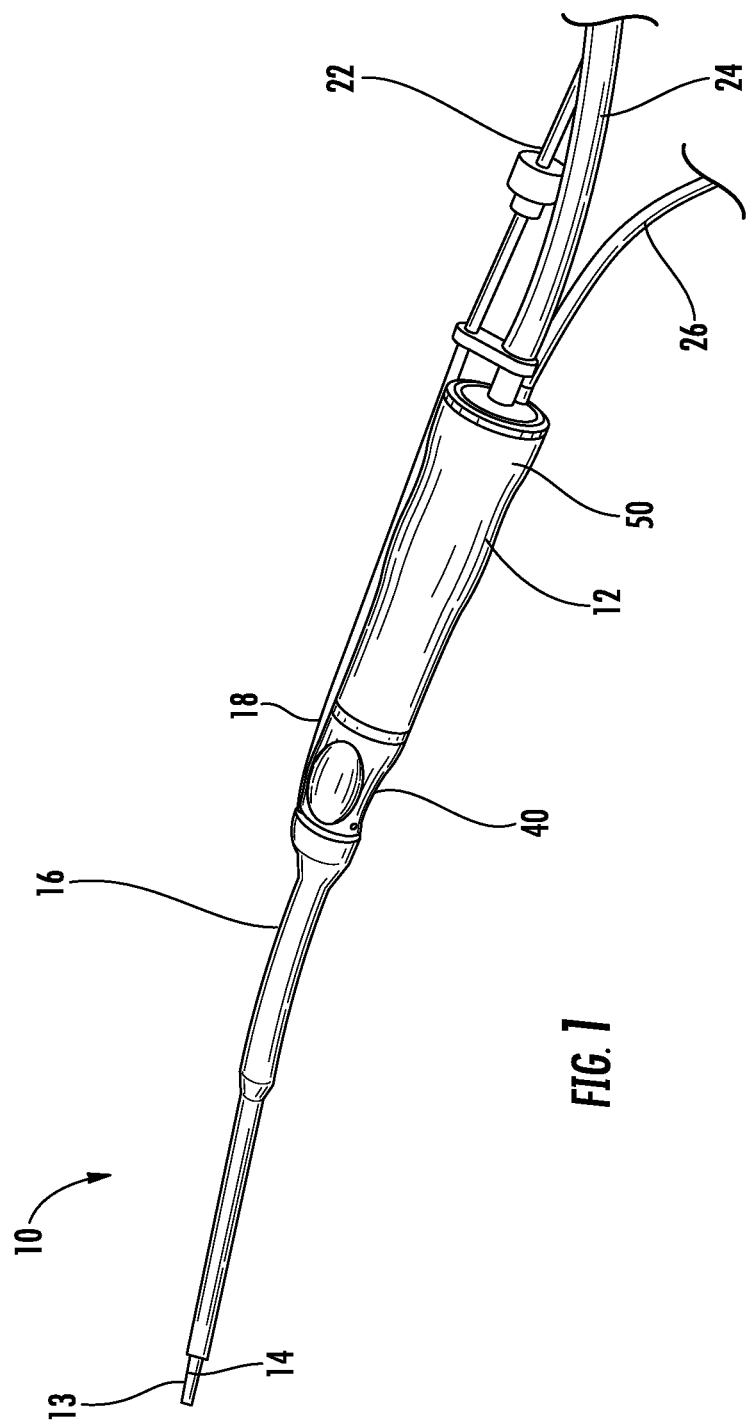
FIG. 1 is a perspective view of an ultrasonic apparatus in accordance with embodiments of the present invention.

Embodiments of the presently disclosed connectors for surgical handpieces will now be described in detail with reference to the drawings, in which like reference numerals designate identical or corresponding elements in each of the several views. As used herein, the term "distal" refers to that portion of the instrument, or component thereof which is farther from the user while the term "proximal" refers to that portion of the instrument or component thereof which is closer to the user during normal use. The terms "ultrasonic horn," "ultrasonic tip," "ultrasonic surgical tip," "surgical tip", "horn" and "tip" are used herein interchangeably.

Figure 2:
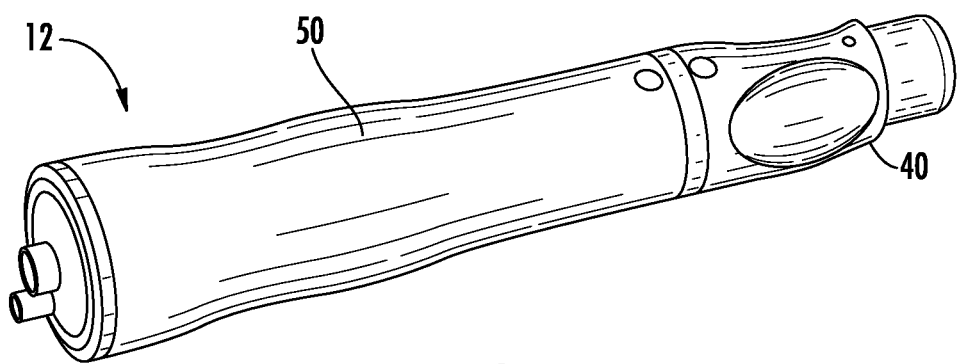
FIG. 2 is a perspective view of a handpiece with a nosecone in accordance with embodiments of the present invention.
Figure 3:
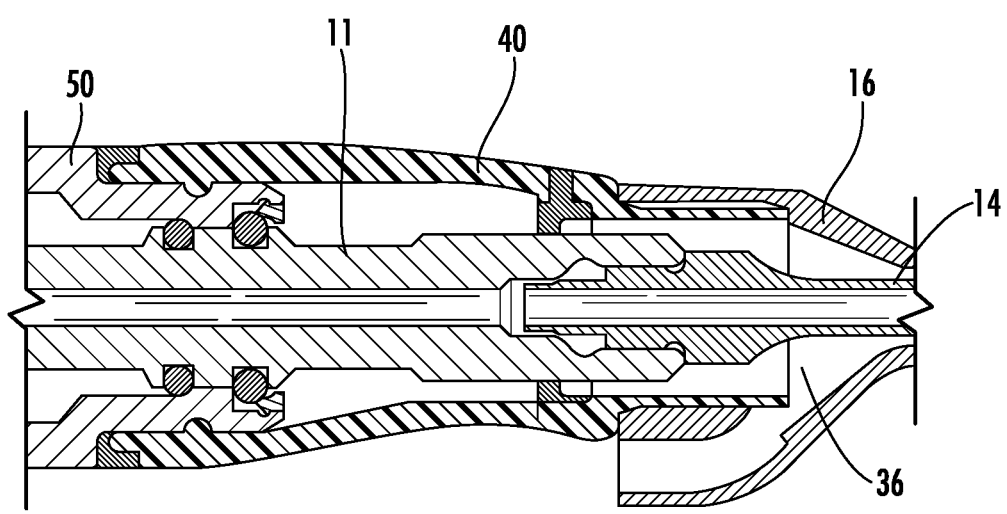
FIG. 3 is a longitudinal-sectional view of a portion of the ultrasonic apparatus of FIG. 1.

Referring now to FIGS. 1-3, one embodiment of the presently disclosed apparatus for ultrasonically fragmenting and aspirating tissue is shown. Generally an ultrasonic surgical apparatus 10 includes a handpiece 12 for use by a surgeon to direct fragmentation. The handpiece 12 encases a transducer (not shown) on which a surgical tip or ultrasonic horn 14 is fastened. The ultrasonic horn can be powered by the transducer and be ultrasonically actuated to fragment tissue and suction effluent via a central channel. A distal end portion 13 of the ultrasonic horn 14 extends beyond a distal end of a flue 16. Ultrasonic horn 14 is vibrated to fragment tissue during surgery. The ultrasonic horn may be made of titanium or other conventional materials known in the art.

A cooling and irrigation system which provides cooling fluid to the ultrasonic horn 14 is provided for maintaining temperature within an acceptable range. The handpiece 12 includes a housing 50, which may be formed of a sterilizable plastic, metal or other suitable materials or a combination thereof. The flue 16 provides a path for irrigation fluid or liquid and connects to the distal end of the handpiece 12. The flue 16 typically connects to the handpiece 12 via a nosecone 40. The flue 16 may include or attach to a flue tube 18. The nosecone 40 connects to the housing 50 and covers the internal ultrasonic horn 14.

An irrigation tube 22 connects to the flue tube 18 upstream and supplies irrigation fluid through the flue tube 18 to an operative site during surgery. An aspiration tube 24 provides suction and a path for aspiration from the operative site to a collection canister (not shown). Alternatively, the aspiration tube may be mounted outside of the housing 50. An electrical cable 26 provides power to the apparatus or provides switching connections.

Figure 4:
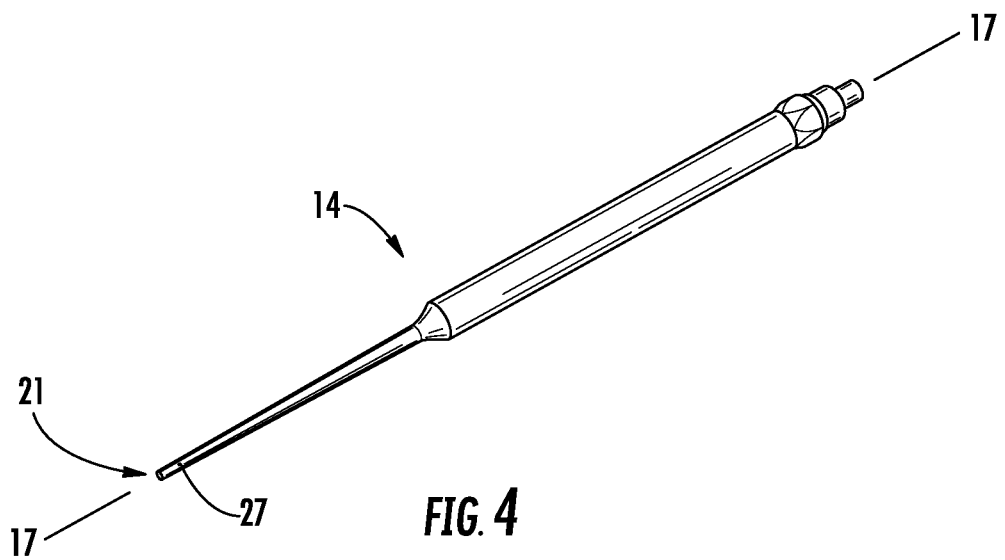
FIG. 4 is a perspective view of an ultrasonic horn.
Figure 5:
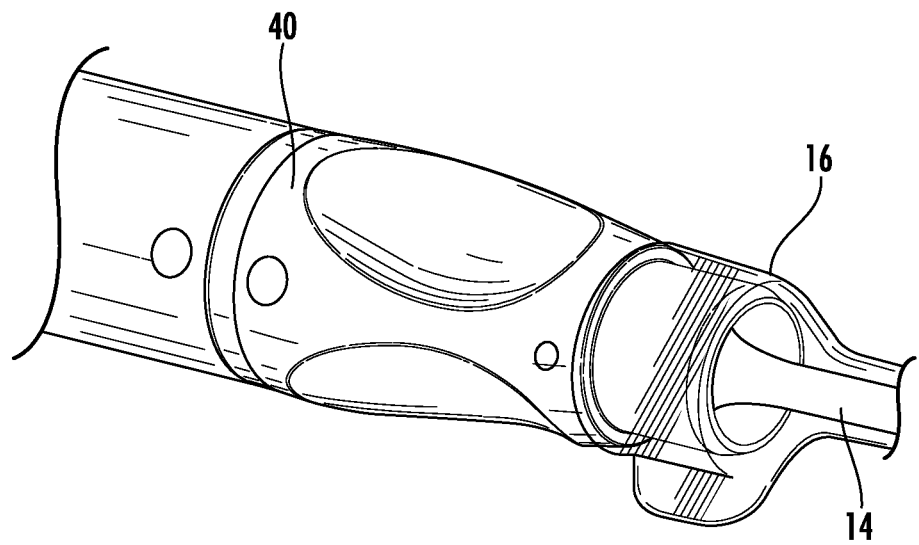
FIG. 5 is a perspective view of a nosecone fully assembled to a handpiece and supporting a flue (the flue tube is not shown in this drawing)
Figure 6:
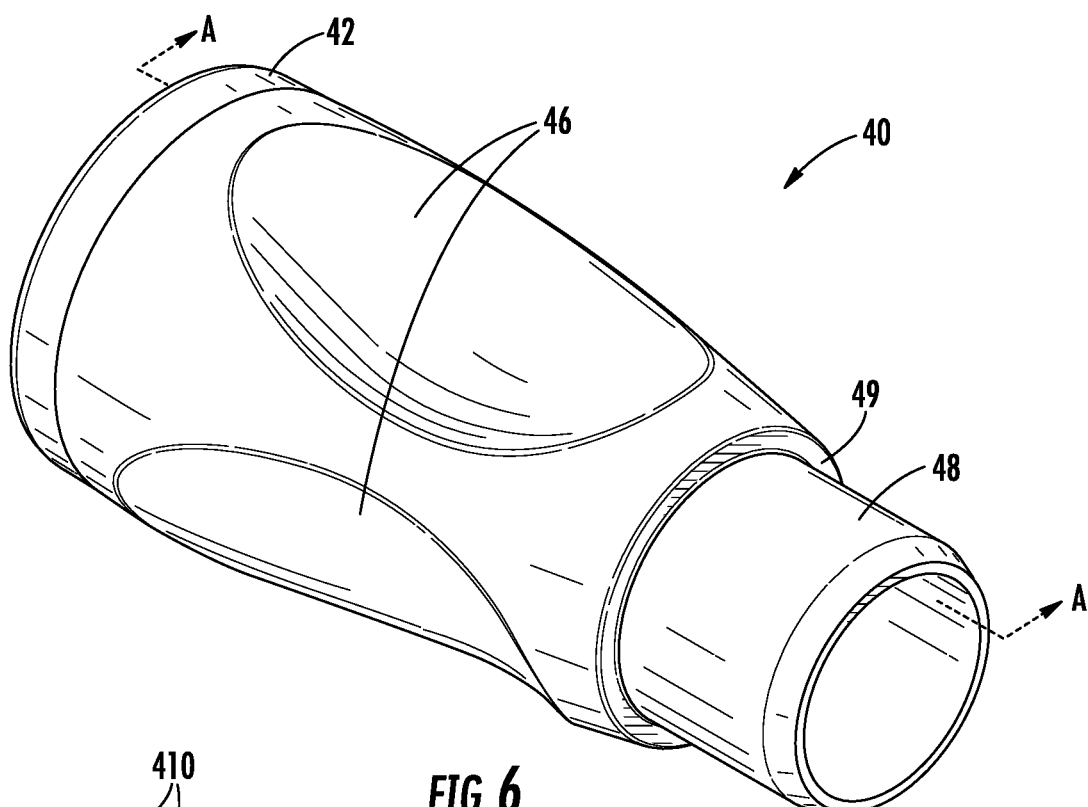
FIG. 6 is a perspective view of a nosecone in accordance with embodiments of the present invention.

FIG. 4 illustrates an embodiment of an ultrasonic tip or ultrasonic horn 14, which is suitable for use with the above-described ultrasonic surgical apparatus for fragmenting and aspirating tissue. The ultrasonic horn has a throughbore 17 and a preaspiration hole or transverse bore 27. Although the ultrasonic horn as shown is a stepped horn, it is known that there are ultrasonic horns that are not stepped.

The ultrasonic horn 14 is substantially circular and disposed within the flue 16. During operation of the ultrasonic apparatus 10, irrigation fluid is supplied through the irrigation tube 22 and flue tube 18 into the flue 16. The flue 16 and the ultrasonic horn 14 define an annular cavity 36 therebetween. Irrigation fluid is supplied from flue 16 through the annular cavity 36 to the distal end of the ultrasonic horn 14. A transverse bore is formed in preaspiration holes 27 near the distal end of the ultrasonic horn 14 and communicates with the throughbore 17. The irrigation fluid is drawn from preaspiration holes 27 and the surgical site into an inlet 21 of the throughbore 17 along with fragmented tissue, blood, etc., and is removed from the surgical site via the throughbore 17 and the aspiration tube 24. The transverse bore provides an alternate route for fluid to enter throughbore 17 when inlet 21 becomes clogged. The nosecone 40 attaches to the housing 50 and covers internal portion of the ultrasonic horn 14.

In a more detailed aspect, irrigation liquid, for example saline, is necessary to cool the surgical tip and site of tissue fragmentation. This irrigation liquid may be provided to the flue with a peristaltic pump at a rate as low as 2 to 3 ml/min, which is only typically about a drip or two a second. The irrigation liquid is supplied at the proximal end of the ultrasonic horn. The irrigation liquid progresses to near the distal end of the ultrasonic horn, where two preaspiration holes, which may each have a 0.015 inch diameter for example, suction a majority, perhaps 90-95%, of the irrigation through the holes connecting the outside horn diameter to the central suction channel. This action of irrigation and suction supports a contiguous cooling circuit for the vibrating titanium metal and it also helps to wet effluent such as blood and tissue in the central channel. Some irrigation is also favorable to cooling the surgical site, improving coupling to tissue, and affording cavitation necessary to emulsification and aspiration of tissue, such as tumors.

The nosecone 40 will be described in more detail with reference to FIGS. 6-17. The form of the nosecone is generally a cylindrical taper having a generally circular cross-section and a neck 48 at the narrower end of the taper. The tapered nosecone body transitions to the neck 48 through a nosecone shoulder 49. The neck 48 has a constant diameter that is smaller than the diameter of the narrower end of the taper. The neck 48 may have a beveled end 480. It provides a surface area for holding the flue 16. Alternatively, the nosecone may be substantially cylindrical and may have a cross-section that is generally oval or of another suitable shape.

The nosecone 40 may have a plurality of recessed lobes 46 on the outer surface. The lobes are circumferentially spaced, symmetrically or asymmetrically, about a longitudinal axis. The recessed lobes 46 may each have a recessed area of a shape suitable to be grasped by a user with fingers. For example, the recessed area may be oval or circular. In an exemplary embodiment, along the tapered section, three lobes, 120 degrees apart, provide finger grip placement. The tri-lobe configuration on the outer surface of the nosecone provides an ergonomic hand grip area that makes it easy for a user to grasp and hold the handpiece in hand and thus enhances comfort for the user.

An internal overmold portion 44, located proximal to the neck 48, serves as a primary fluid seal. The overmold portions eliminate the need for O-rings and thus enhance ease of assembly. The overmolding may be made from a medically comparable thermoplastic elastomer, for example polypropylene or other conventional materials used in gaskets, stoppers and seals as known in the art. A thermoplastic elastomer is a plastic polymeric material that becomes pliable or moldable above a specific temperature and solidifies upon cooling. The materials of the nosecone body and overmold portions are selected for adequate adherence and withstand of sterilization. Once fully assembled, the internal overmold portion 44 of the nosecone 40 conforms to the internal ultrasonic horn 14 to prevent fluid ingress into the handpiece 12.

The nosecone 40 has an end overmold portion 42 at the large diameter open end. The end overmold portion 42 is a part of the coupling mechanism that affixes the nosecone 40 to the housing 50. The coupling mechanism can be used not only for connecting the housing and nosecone components of surgical handpieces, but also for attachment of members of other medical devices or other apparatus.

Turning now to FIGS. 18-23, in a general aspect, embodiments of the present invention may provide a connection apparatus 30 for attachment of members of a medical device. The connection apparatus 30 comprises a first member, for example, a nosecone 40, and a second member, for example, a housing 50. The first member or nosecone 40 has a first body 411 and a first connecting section 412. The first member or nosecone may further comprise a lip 410 extending from the first connecting section (or nosecone connecting section) 412. The first connecting section has a first end face 413 and an inner surface 414. The second member or housing 50 has a second body 57, a second connecting section (or housing connecting section) 52 and a shoulder 54 at the junction between the second body 57 and the second connecting section 52. The second connecting section has a second end face 58 and an outer surface 59 shaped for telescoping into the inner surface of the first connecting section 412. The outer surface 59 comprises a groove 56 extending from the second end face 58 towards the shoulder 54. The groove 56 may be a curved or angled groove, such as a J-shaped groove, forming a moving track for the nub 43, with a rest position 560 at the end of the track, located between the shoulder 54 and the second end face 58. The first member or nosecone 40 comprises a nub 43 on the inner surface 414 extending radially inward for engaging the groove 56. The first member or nosecone 40 has an end overmold portion 42 at least partially covering the first end face and positioned to bear against the shoulder 54, whereby the end overmold portion 42 is compressed between the first body 411 and the second body 57.

The J-shaped groove may comprise a plurality of segments. For example, it may have three segments. The first segment extends from the second end face of the housing towards the shoulder of the housing and is generally perpendicular to the second end face. The second segment is at an angle relative to the first segment, for example, at an angle of about 15 to about 75 degrees, and preferably between about 30 to about 60 degrees. The third segment constitutes the rest position, which is shorter than the first segment and the second segment. It may be at an angle relative to the second segment. It is contemplated that the rest position may simply be the end of the second segment without being at any apparent angle relative to the second segment.

Figure 7:
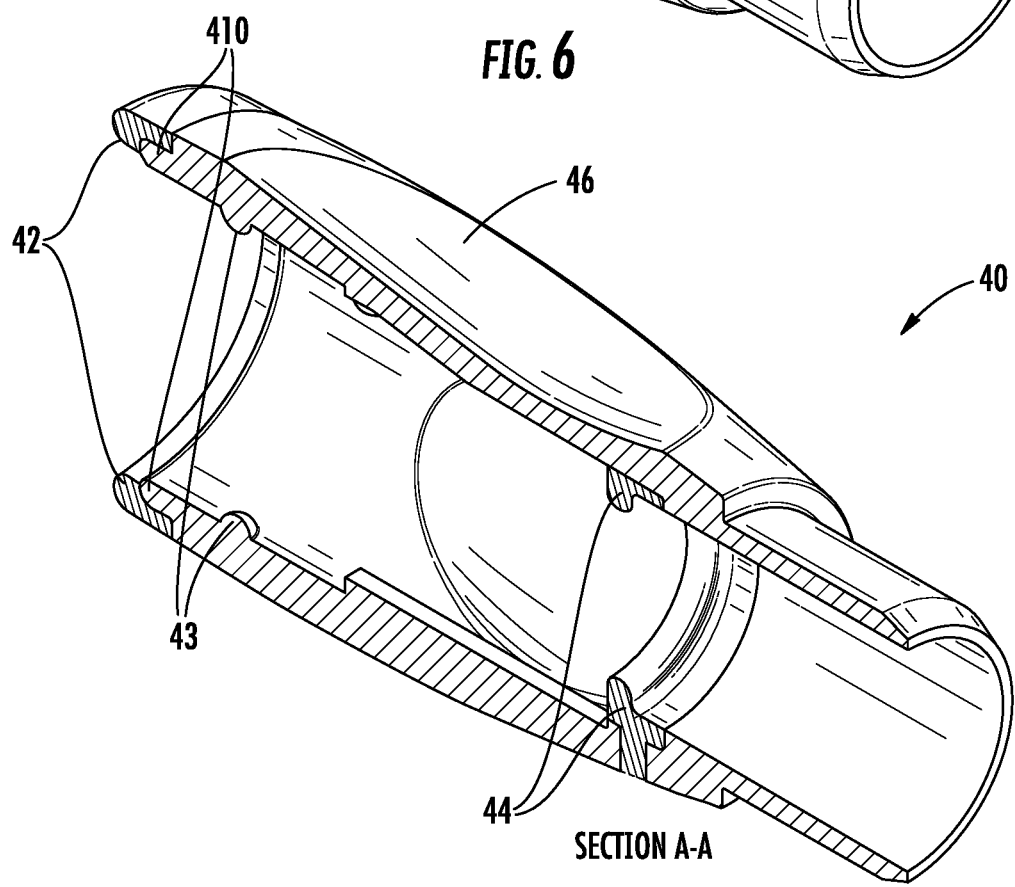
FIG. 7 is a cross-sectional view taken along line A-A of FIG. 6.
Figure 8:
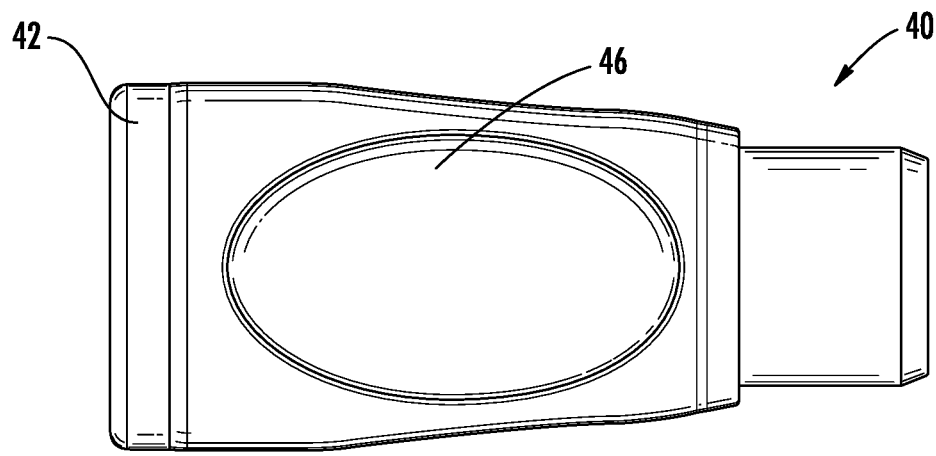
FIG. 8 is a top plan view of the nosecone of FIG. 6.
Figure 9:
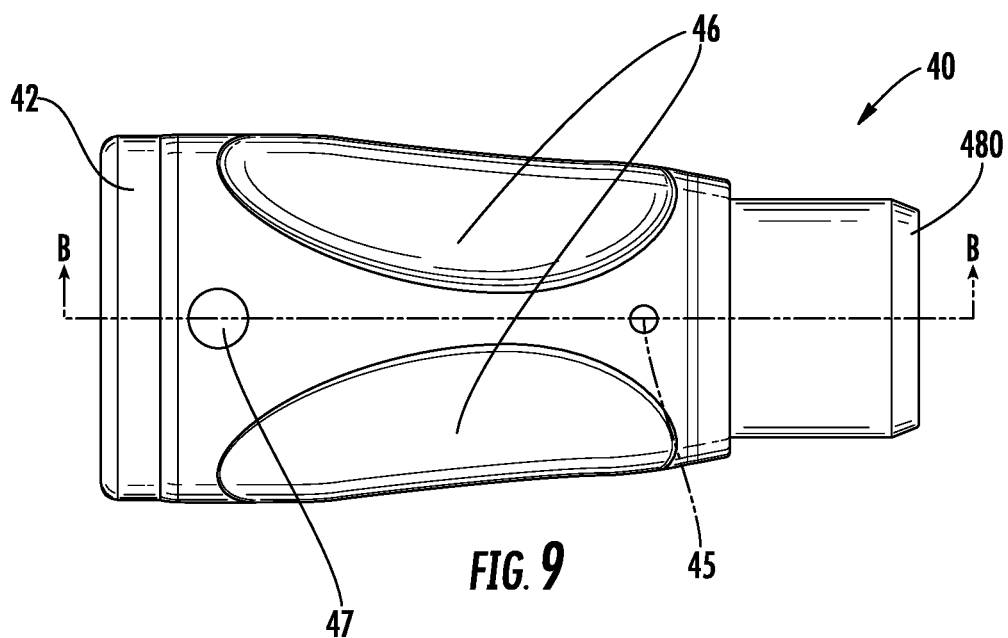
FIG. 9 is a bottom plan view thereof.
Figure 13:
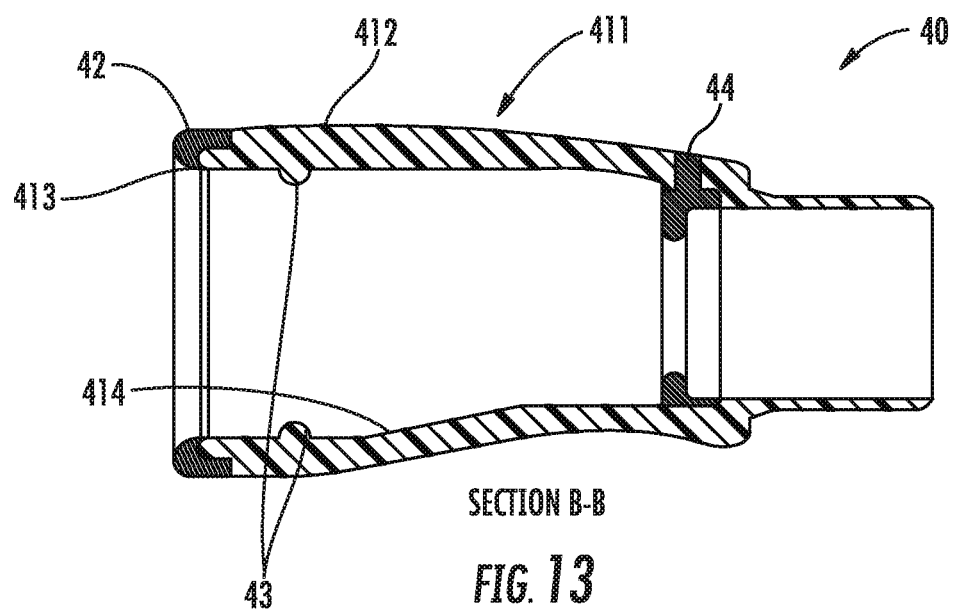
FIG. 13 is a cross-sectional view taken along line B-B of FIG. 9.
Figure 14:
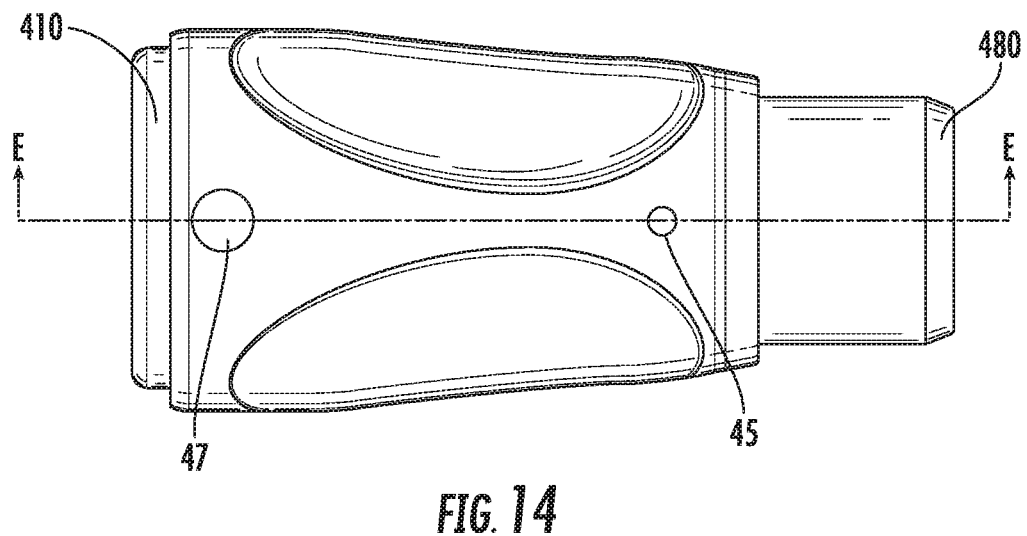
FIG. 14 is a bottom plan view of the nosecone of FIG. 6 without the overmold portions.
Figure 15:
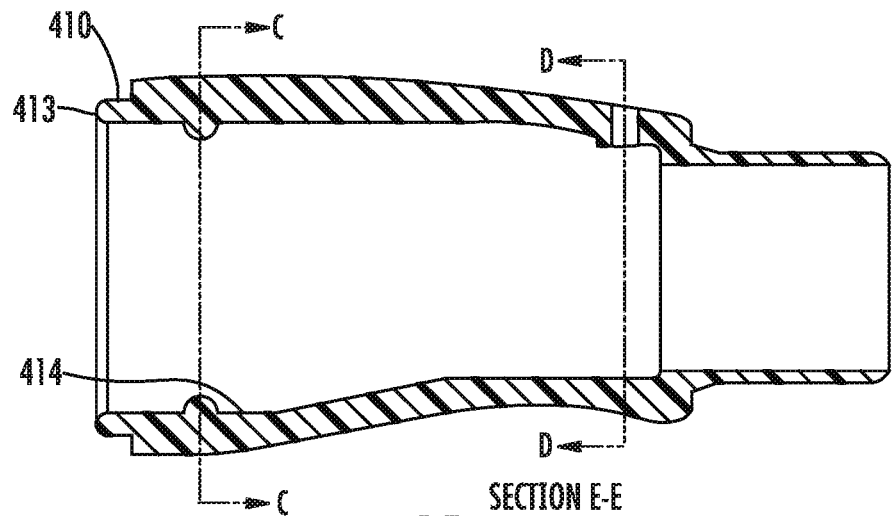
FIG. 15 is a cross-sectional view taken along line E-E of FIG. 14
Figure 16:
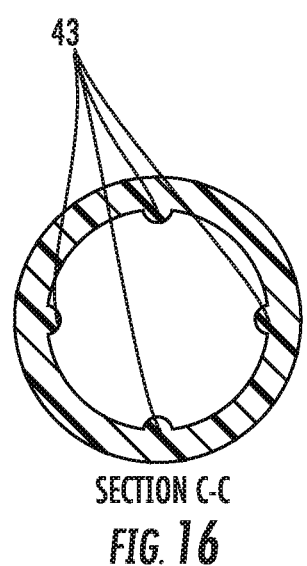
FIG. 16 is a cross-sectional view taken along line C-C of FIG. 15
Figure 17:
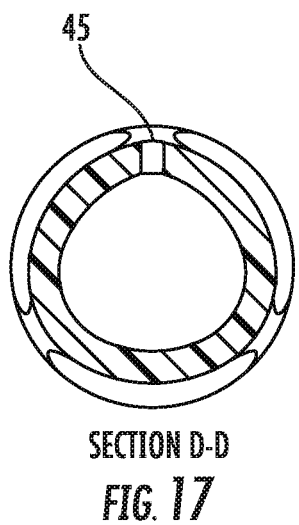
FIG. 17 is a cross-sectional view taken along line D-D of FIG. 15
Figure 18:
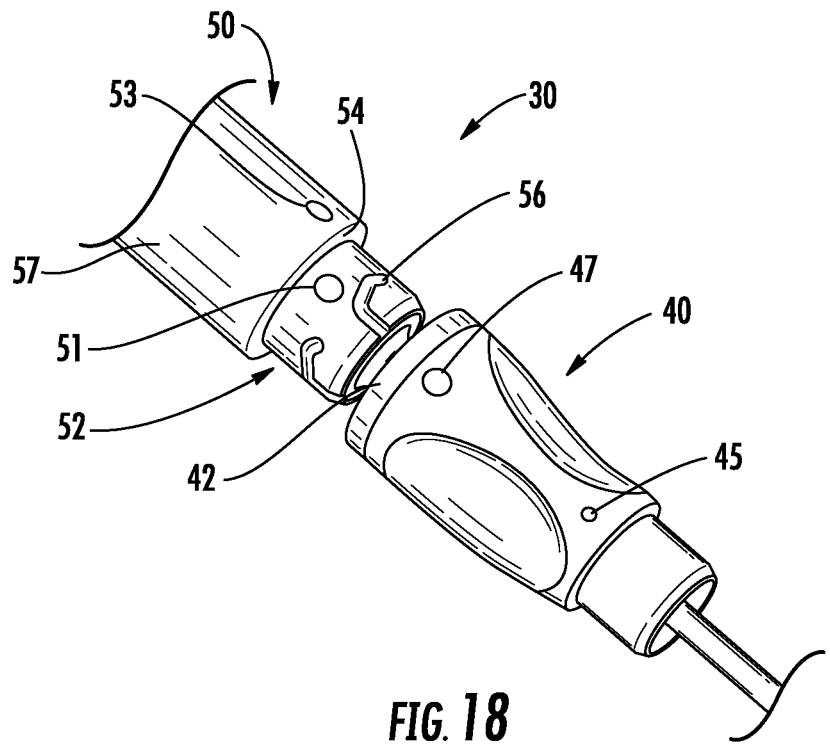
FIG. 18 shows the handpiece housing and nosecone in a dissembled state.
Figure 19:
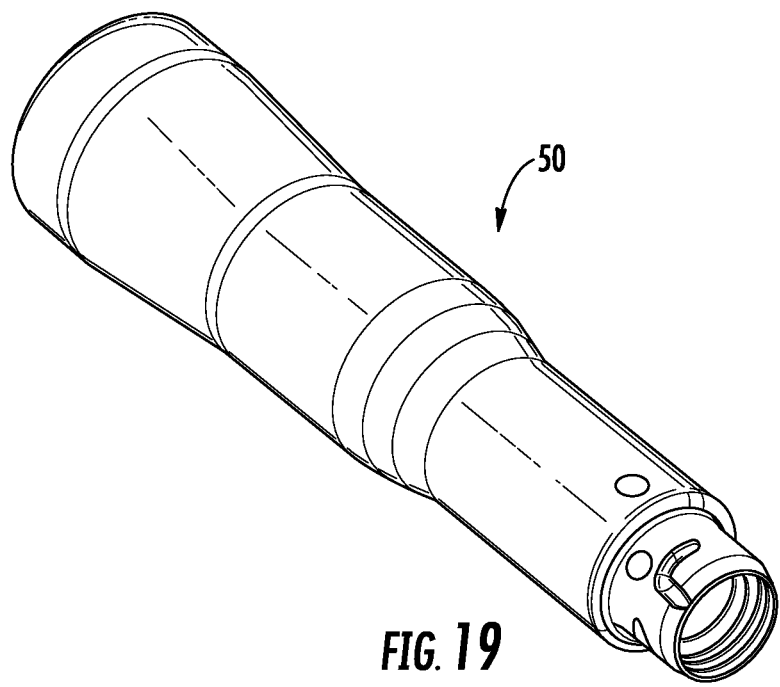
FIG. 19 is a perspective view of the handpiece housing.
Figure 20:
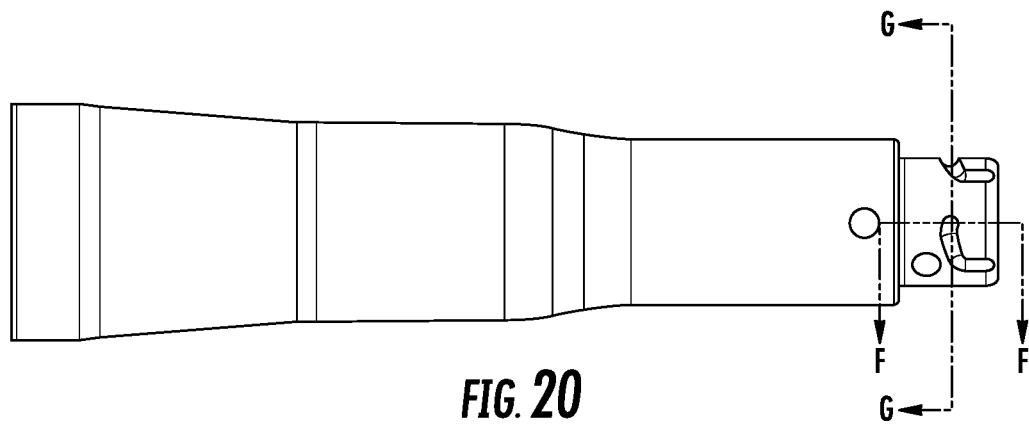
FIG. 20 is a side view of the handpiece housing of FIG. 19.
Figure 21:
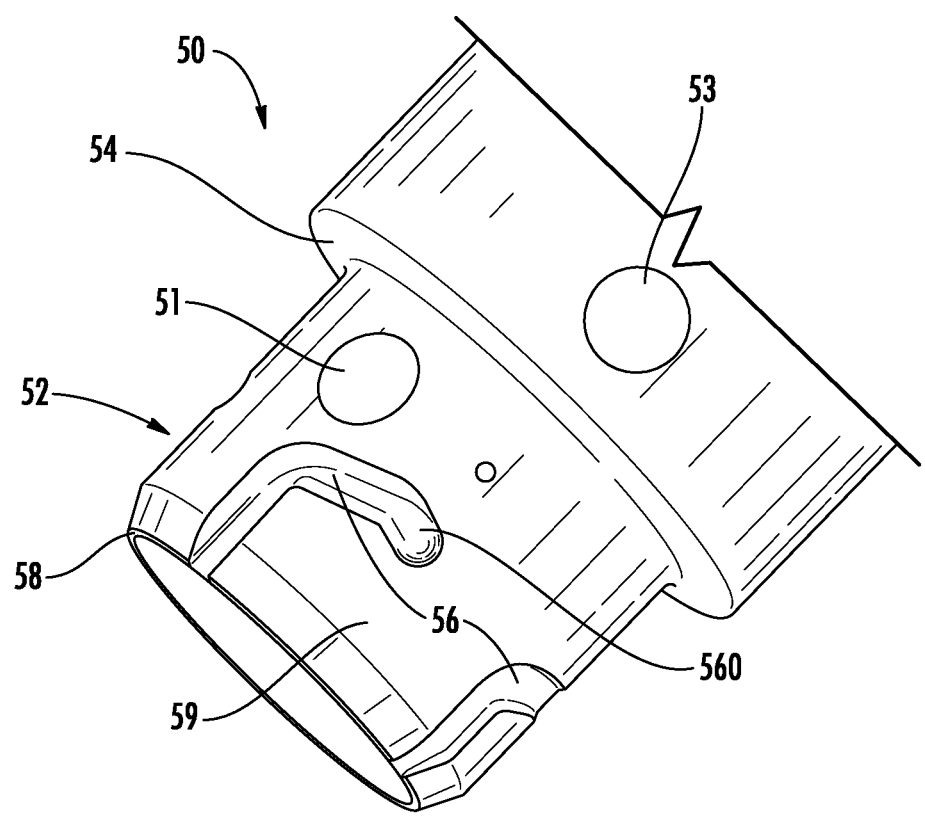
FIG. 21 is an enlarged perspective view of the distal end of the handpiece housing of FIG. 19.

The end overmold portion 42 may be present on the outer diameter or inner diameter of the nosecone connecting section or both diameters. If a lip 410 exists on the nosecone, the end overmold portion may be present on the outer diameter of outer diameter or inner diameter of the lip 410 or both diameters. In the exemplary embodiment as shown in FIG. 7, the end overmold portion 42 is positioned at least partially on the outer diameter of the lip 410 and flush with the outer surface of the nosecone 40.

The first member 40 may have more than one nub on the inner surface 414, arranged radially about the first connecting section 412, and the second member 50 may have more than one groove 56 on the outer surface arranged radially about the second connecting section 52. The nubs 43 may be spaced symmetrically or asymmetrically apart, and the grooves are spaced accordingly such that each nub is positioned to engage with a respective groove. In the exemplary embodiment as shown, the first member 40 has four nubs 43 on its inner surface evenly spaced approximately 90 degrees apart, and the second member 50 has four grooves 56 on its outer surface evenly spaced approximately 90 degrees apart.

In the embodiment as shown, the first member is a nosecone and the second member is a surgical handpiece housing. It is contemplated that the first member may be a surgical handpiece housing and the second member may be a nosecone.

In operation, a user positions each nub 43 to engage a respective groove 56 and moves each nub 43 in the groove 56 towards the shoulder 54 of the housing 50 until the end overmold portion 42 contacts the shoulder 54. The grooves may be generally evenly spaced apart on the housing about a longitudinal axis. Likewise, the nubs may be generally evenly spaced apart on the inner surface of the nosecone about a longitudinal axis accordingly for engaging the grooves on the housing.

The inside of the nosecone is hollow to provide clearance space in order for it to slip over the ultrasonic horn 14 and connect to the housing 50. In the exemplary embodiment as shown in the drawings, four nubs 43, in the form of spheres that are about 0.06 inches in diameter, form part of the coupling mechanism that affixes the nosecone 40 to the housing 50. The spheres may have a diameter in the range of about 0.01 to about 0.10 inches, for example, in the range of about 0.2 to about 0.8 inches. The nubs may be in the form of other raised structures suitable for engaging with the grooves.

The overmold portions are preferably made of a material that has elastomeric properties of having a low Young's Modulus and flexibility. A proper material should also be able to achieve a strong, stable bond to the substrate. It also needs to be able to be injected into a mold in a semi-fluid or fluid state at an elevated temperature and to remain on the substrate and retain its strength and provides elasticity after it has cooled and solidified. In a preferred embodiment, the body of the nosecone is made from glass-filled polypropylene (PP) which has appropriate strength, stiffness, melting temperature and ability to adhere with overmold material (thermoplastic elastomer). In another preferred embodiment, the overmolding is made from a healthcare thermoplastic elastomer grade used in gaskets, stoppers and seals. It has the ability to bond to a variety of substrates, for example PP. Compression set, reseal capability, and an ability to be sterilized under autoclave and ethylene oxide are some of the factors to be considered in selecting materials for the design.

There are several identification markers on the apparatus for the coupling mechanism. The housing has a housing identification marker 53 on the housing body 57 and another connection identification marker 51 on the housing connecting section 52. The nosecone 40 has a nosecone identification marker 47. The identification markers may be in any form, shape and color as desired, such as white dots.

Figure 24:
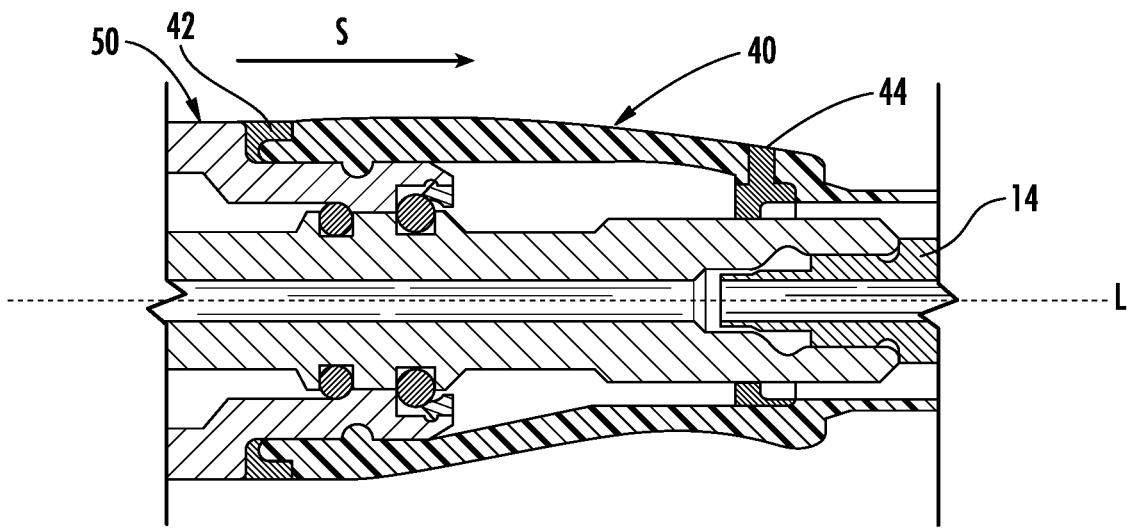
FIG. 24 is a partial longitudinal-sectional view of the handpiece housing and nosecone in an assembled state.
Figure 25:
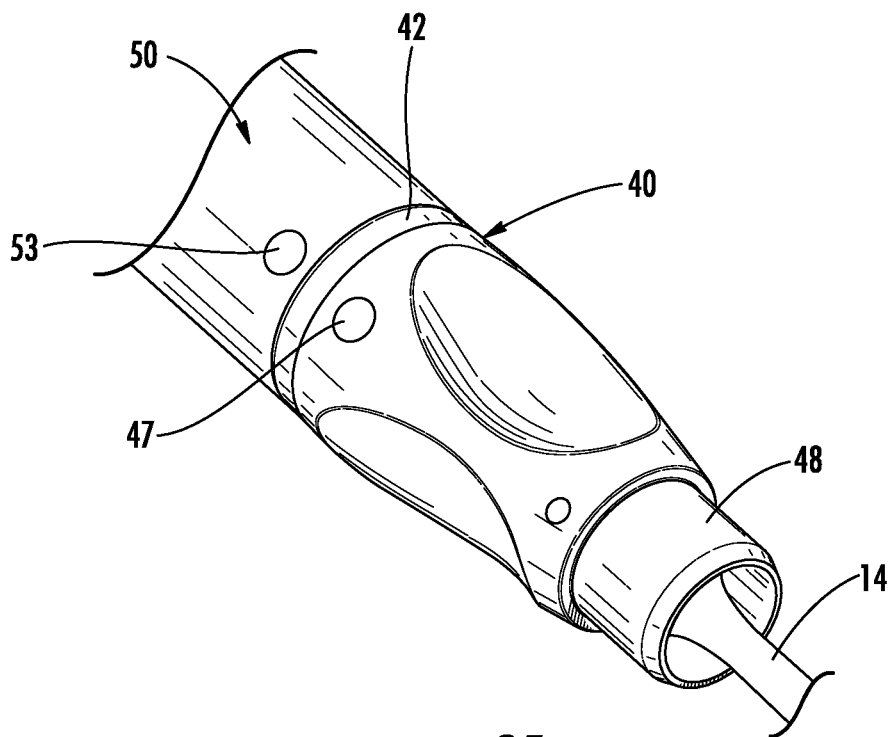
FIG. 25 is a perspective view of a portion of the handpiece housing and nosecone in an assembled state.

Referring now to FIGS. 24 and 25, attaching the nosecone in some embodiments of the present invention is simple because the user only needs to install one component without the need for handling separate O-rings. Once an ultrasonic horn 14 has been torqued to a handpiece 12, the nosecone 40 can be slipped over the ultrasonic horn 14. As the nosecone approaches the housing connecting section 52 of the housing 50, the nosecone identification marker 47 on the nosecone 40 should be oriented to align with the connection identification marker 51 on the housing connecting section 52 of the housing 50. This essentially guides the nosecone nubs 43 to the grooves 56 in the housing 50.

Once the nub 43 has joined the groove 56 of the housing 50, it will follow along and rotate clockwise through the J-shaped track until it reaches the rest position 560, where the end overmold portion 42 compresses. Depending on the orientation of the grooves, the nosecone may travel for a degree to lock. In the exemplary embodiment as shown in FIG. 23, the nosecone travel for about 42 degrees in the grooves to lock.

The nosecone 40 remains fixed in the rest position 560 by means of the expanding of the end overmold portion 42. As shown by arrow S, the end overmold portion 42 acts as a spring, applying a linear force to drive the nub 43 against the end of the groove 56. Locking of nosecone 40 is achieved via elastomer expansion that pushes the nub 43 to contact the wall of the groove 56, for example, the wall in the rest position 560. The flexible property of the thermoplastic material of the end overmold portion 42 works like a spring, expanding out in the longitudinal axis L which results in a linear force to drive the nosecone nubs 43 against the wall at the end of the grooves 56 of the handpiece housing 50 to secure the nosecone firmly to the handpiece.

Although preferably the end overmold portion 42 is an annular piece, it does not have to be a complete annulus. It may have one or more gaps in the ring-shaped structure so long as the end overmold portion provides a spring force that allows locking of the housing 50 and the nosecone 40.

FIG. 25 shows alignment of the housing identification marker 53 on the housing 50 and the nosecone identification marker 47 on the nosecone 40 in fully coupled state. The coupling mechanism is verified to the user via the alignment of the nosecone identification marker 47 to the housing identification marker 53. Once fully assembled, the internal overmold portion 44 conforms to the internal horn 11 and forms a fluid seal to prevent fluid ingress into the handpiece 12.

The internal overmold portion 44 on the inner surface of the nosecone 42 is positioned radially about the nosecone 42 to provide a fluid tight seal that prevents ingress of irrigation fluid into the housing. In addition, the internal overmold portion 44 enables keeping the flue primed, as the surgeon puts the handpiece down on the patient or a table during surgery. The inner seal helps keep the flue primed or irrigation functional immediately, when the handpiece is picked back up by the user. The inner seal reduces the volume that the trickle of irrigation could fill if the system were laid down with the tip up slightly. The inner seal helps keep the liquid in the flue to tip space until use.

An insert molding method can be used for manufacturing the nosecone in some embodiments of the present invention. In the manufacturing method, a premolded insert is placed into the mold before a thermoplastic material is shot. After the mold assembly is in place, the overmold material is then injected into the mold, either in a semi-fluid or fluid state, using conventional methods known in the art. For making the internal overmold portion, the thermoplastic material can be injected through an opening 45. The manufacturing of the nosecone could be highly economical, such that a mold of the nosecone matrix or substrate is followed by overmolds in a single tool with two or more actuations as needed. The nosecone with overmold portions could be supplied as a disposable, greatly enhancing ease-of-use with simple assembly in the operating room.

Although the exemplary embodiments of the present invention show the end overmold portion and the internal overmold portion as two separate elements, it is contemplated that the two elements may be two portions of a single piece. The nosecone may have a single overmolded piece that includes an end overmold portion, an internal overmold portion, and a connecting overmold portion that connects the end and internal overmold portions. The connecting overmold portion may be on the inner surface or the outer surface of the nosecone. For example, the nosecone may have an elastomer encased body as a single piece which comprises an end overmold portion, an internal overmold portion, and an elastomer wall on the outer surface of the nosecone. In addition, the elastomer may form part of the nosecone body.

Although one embodiment of the present invention is illustrated with a J-lock clasp in the handpiece, it is contemplated that the end overmold portions can work with other connecting, coupling or interlocking mechanisms in which O-rings or gaskets are used or desired, such as locking teeth, snap-ears, other snap-in locking features, and other mechanisms. The spring force or seal function necessary to such a connecting, coupling or interlocking mechanism can be achieved through applying an overmolding technology as described in the embodiments of the present invention.

The connection apparatus embodiments of the present invention is useful for attachment of components in machines, apparatuses, instruments and devices including but not limited to medical devices. The nosecone embodiments of the present invention can be applied to various surgical handpieces, such as CUSA Excel 36 kHz and 23 kHz ultrasonic handpieces and other surgical handpieces. The overmolding technology can be applied on longer angle adapted nosecones as well including longer shroud nosecones with angled sections. A person skilled in the art could envision similar requirements and solutions using the basic idea of the embodiments of the present invention. It is contemplated that one, two, or more overmolds may be used depending on the geometry of the handpiece and the needs for sealing and/or connection.

The nosecone in some embodiments of the present invention may eliminate user installed O-rings, which are difficult to install for nurses or other users wearing gloves in the sterile field of an operating room. It provides the same critical sealing functionality without cumbersome installation. It eliminates the possibility to install O-rings incorrectly or in the wrong place, and eliminates the problem of assembling the wrong O-rings to surgical tip packs. It also enables a low cost disposable component created in two actuations of a single molding tool, and enhances ability to provide a clean and sterilized component to the operating room. The nosecone in some embodiments of the present invention improves ease of use in assembly, and provides easy and flawless assembly while maintaining functionality. It also enables a clean and sterile component for patient protection in the operating room.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The embodiments may be embodied in other forms without departure from the scope and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention.

We claim:

1. A connection apparatus for attachment of members of a medical device, comprising:
    a first member having a first end and an opposing second end, wherein the first end of the first member includes a first body and the opposing second end of the first member includes a first connecting section, and wherein the first body includes a neck, wherein the first connecting section and the first body define an inner surface through the first member, wherein the first connecting section has a first end face and an end overmold portion, and wherein the first body further includes an internal overmold portion positioned radially about the inner surface of the first body adjacent the neck;
    a second member having a second body, a second connecting section and a shoulder at a junction between the second body and the second connecting section, the shoulder having a longitudinal surface, the second connecting section having a second end face and an outer surface shaped for telescoping into the first connecting section, the outer surface having a groove extending from the second end face towards the shoulder;
    wherein the first member has a nub on the inner surface extending radially inward for engaging the groove; and
    wherein the end overmold portion is overmolded onto and at least partially covers the first end face of the first connecting section and is positioned to bear against the longitudinal surface of the shoulder of the second member, whereby the end overmold portion is compressed between the first connecting section and the longitudinal surface of the shoulder of the second member.

2. The connection apparatus of claim 1, wherein the first member has more than one nub on the inner surface arranged radially about the first connecting section, and the second member has more than one groove on the outer surface arranged radially about the second connecting section, and each nub is positioned to engage with each groove.

3. The connection apparatus of claim 1, wherein the end overmold portion is made of a thermoplastic elastomer.

4. The connection apparatus of claim 1, wherein the first member is a nosecone and the second member is a surgical handpiece housing.

5. The connection apparatus of claim 1, wherein the groove is J-shaped.

6. The connection apparatus of claim 1, wherein the nub is sphere-shaped.

7. The connection apparatus of claim 1, wherein the internal overmold portion is made of a thermoplastic elastomer.

8. The connection apparatus of claim 1, wherein the end overmold portion is made of a second shot of material overmolded onto the first end face made of a first shot of material, wherein the first shot of material is different from the second shot of material.

9. The connection apparatus of claim 1, wherein the end overmold portion is flush with an outer surface of the first member.

* * * * *